US009623025B2

(12) United States Patent
Supuran et al.

(10) Patent No.: US 9,623,025 B2
(45) Date of Patent: Apr. 18, 2017

(54) TREATMENT OF MAMMALIAN DISORDERS MEDIATED BY ALPHA-CARBONIC ANHYDRASE ISOFORMS

(76) Inventors: Claudiu Supuran, Florence (IT); Seppo Parkkila, Narva (FI)

( * ) Notice: Subject to any disclaimer, the term of this patent is extended or adjusted under 35 U.S.C. 154(b) by 247 days.

(21) Appl. No.: 13/375,946

(22) PCT Filed: Jun. 1, 2010

(86) PCT No.: PCT/EP2010/057598
§ 371 (c)(1),
(2), (4) Date: Dec. 2, 2011

(87) PCT Pub. No.: WO2010/139678
PCT Pub. Date: Dec. 9, 2010

(65) Prior Publication Data
US 2012/0088776 A1  Apr. 12, 2012

(30) Foreign Application Priority Data
Jun. 2, 2009  (EP) .................................... 09161720

(51) Int. Cl.
*A61K 31/506*  (2006.01)
*A61K 45/06*  (2006.01)
(52) U.S. Cl.
CPC ............ *A61K 31/506* (2013.01); *A61K 45/06* (2013.01)
(58) Field of Classification Search
CPC ................................ A61K 31/506; A61K 45/06
See application file for complete search history.

(56) References Cited

U.S. PATENT DOCUMENTS

2005/0244475 A1 * 11/2005 Edelman .............. A61K 9/0051
424/427

FOREIGN PATENT DOCUMENTS

| WO | WO 9730701 A2 * | 8/1997 |
| WO | WO 9903854 A1 * | 1/1999 |
| WO | 03072090 | 9/2003 |
| WO | WO 2004005281 A1 * | 1/2004 |

OTHER PUBLICATIONS

Dodgson et. al., Epilepsia, 2000, International League Against Epilepsy, vol. 41, suppl. 1, pp. S35-S39.*
Lee et. al., Epilepsia, 2003, International League Against Epilepsy, vol. 44, issue 3, pp. 339-347.*
Soininen et. al., Dementia and Geriatric Cognitive Disorders, 2007, S. Karger AG, vol. 23, pp. 8-21.*
Weber et. al., Journal of Medicinal Chemistry, 2004, American Chemical Society, vol. 47, pp. 550-557.*
Thuile et. al., Psychiatry and Clinical Neurosciences, 2006, Folia Publishing Society, vol. 60, p. 394.*
Supuran, Nature Reviews Drug Discovery, Jan. 2008, Nature Publishing Group, vol. 7, pp. 168-181.*
Sun et. al., The Journal of Pharmacology and Experimental Therapeutics, 2001, American Society for Pharmacology and Experimental Therapeutics, vol. 297, No. 3, pp. 961-967.*
Sevinc (2009) "Activity of Nilotinib (AMN-107) Alone in Advanced Gastrointestinal Stromal Tumors Progressing on Imatinib and Sunitinib (Case Report)"; Chemotherapy, 55(2): 132-136.
Brownlow et al. (2008) "Comparison of nilotinib and imatinib inhibition of FMS receptor signaling, macrophage production and osteoclastogenesis"; Leukemia: Official Journal of the Leukemia Society of America, Leukemia Research Fund, 22(3): 649-652.
Dogan et al. (2009) "Ocular Side Effects Associated with Imatinib Mesylate and Perifosine for Gastrointestinal Stromal Tumor"; Hematlogy—Oncology Clinics of North America, 23(1): 109-114.
Moen et al. (2007) "Imatinib—A Review of its use in Chronic Myeloid Leukaemia"; Drugs, Adis International Ltd, 67(2): 299-320.
Jabbour et al. (2007) "Drug evaluation: Nilotinib—a novel Bcr-Agl tyrosine kinase inhibitor for the treatment of chronic myelocytic leukemia and beyond"; IDRUGS: The investigational Drugs Journal, 10(7): 468-479.
"Tasigna (nilotinib)—Highlights of Prescribing Information"; Internet Citation (Oct. 2007), 1-12.
Supuran (2008) "Carbonic anhydrases: novel therapeutic applications for inhibitors and activators"; Nature Reviews Drug Discovery, 7: 168-181.
Supuran et al. (2003) "Carbonic Anhydrase Inhibitors"; Medicinal Research Reviews, 23(2): 146-189.
Breccia et al. (2008) "Ocular side effects in chronic myeloid leukemia patients treated with imatinib"; Leukemia Research, 32(7): 1022-1025.

* cited by examiner

*Primary Examiner* — Sarah Pihonak
(74) *Attorney, Agent, or Firm* — Saliwanchik, Lloyd & Eisenschenk

(57) ABSTRACT

The present invention pertains to 4-(4-methylpiperazin-1-ylmethyl)-N-[4-methyl-3-(4-pyridin-3-yl)pyrimidin-2-ylamino)phenyl]-benzamide or a pharmaceutically acceptable salt thereof, or 4-methyl-3-[[4-(3-pyridinyl)-2-pyrimidinyl]amino]-N-[5-(4-methyl-1H-imidazol-1-yl)-3-(trifluoromethyl)phenyl] benzamide or a pharmaceutically acceptable salt thereof, for the treatment of disorders mediated by alpha-carbonic anhydrase isoforms selected from intraocular hypertension (glaucoma), epilepsy, Lennox-Gastaut syndrome, altitude sickness, headaches, neurological disorders and obesity.

20 Claims, No Drawings

TREATMENT OF MAMMALIAN DISORDERS MEDIATED BY ALPHA-CARBONIC ANHYDRASE ISOFORMS

CROSS REFERENCE TO RELATED APPLICATIONS

This application is a 371 of International Application No. PCT/EP2010/057598 filed Jun. 1, 2010.

The invention relates to 4-(4-methylpiperazin-1-ylmethyl)-N-[4-methyl-3-(4-pyridin-3-yl)pyrimidin-2-ylamino)phenyl]-benzamide (also known as "imatinib" [International Non-proprietary Name]) and 4-methyl-3-[[4-(3-pyridinyl)-2-pyrimidinyl]amino]-N-[5-(4-methyl-1H-imidazol-1-yl)-3-(trifluoromethyl)phenyl] benzamide (also known as "nilotinib" [International Non-proprietary Name]) or pharmaceutically acceptable salts thereof, respectively, for the treatment of disorders mediated by alpha-carbonic anhydrase isoforms, to the use of imatinib and nilotinib or pharmaceutically acceptable salts thereof, respectively, in the treatment of disorders mediated by alpha-carbonic anhydrase isoforms, and to a method of treating mammals including humans suffering from disorders mediated by alpha-carbonic anhydrase isoforms.

Inhibitors of carbonic anhydrase (CA) are used for the treatment of intraocular hypertension (glaucoma), epilepsy, Lennox-Gastaut syndrome, altitude sickness, migraine, headaches, gastric and duodenal ulcers, neurological disorders and osteoporosis (Supuran, C. T., Scozzafava, A., Conway, J. (Eds): Carbonic anhydrase—Its inhibitors and activators, CRC Press, Boca Raton (Fla.), USA, 2004, pp, 1-363; Supuran, C. T., Scozzafava, A., Carbonic anhydrase inhibitors and their therapeutic potential, Expert Opin. Ther. Pat., 2000, 10, 575-600; Supuran, C. T., Scozzafava, A., Casini, A., Carbonic anhydrase inhibitors. Med. Res, Rev. 2003, 23, 146-189. CA inhibitors such as topiramate and zonisamide are also effective as antiobesity agents although they are not currently approved for such a use (Supuran, Nature Rev Drug Discov 2008).

Imatinib (as mesylate salt, Glivec™/Gleevec™) blocks the activity of the Bcr-Abl oncoprotein and the cell transmembrane tyrosine kinase receptor c-Kit, Glivec™ is approved for several indications including the treatment on chronic myeloid leukemia (CML) and gastrointestinal stromal tumors (GIST). Nilotinib (Tasigna™) is a second-generation protein tyrosine kinase inhibitor (PTKI) and was approved in 2007 for the treatment of adult patients with chronic-phase and accelerated-phase Philadelphia chromosome-positive (Ph+) CML, resistant to or intolerant of prior treatment that included imatinib. The compound is also being investigated for the treatment of patients with GIST.

It has now been demonstrated, surprisingly, that imatinib mesylate and nilotinib hydrochloride monohydrate inhibit all 13 catalytically active mammalian isoforms CA I-XV with $K_I$s in the range of 4 nM-20 µM. CA I and CA II are the most potently inhibited isoforms ($K_I$s of 4-32 nM).

More specifically, the PTKIs imatinib and nilotinib act as very potent inhibitors of two CA isozymes, i.e., human CA I (hCA I) and II (hCA II), with inhibition constants in the range of 4.1-31.9 nM. The isoform with the highest affinity for these two compounds is the ubiquitous, physiologically dominant hCA II. In fact, the clinically used sulfonamide inhibitor par excellence, acetazolamide has a $K_I$ of 12 nM against hCA II, intermediate between that of nilotinib ($K_I$ of 4.1 nM) and imatinib ($K_I$ of 30.2 nM). The second cytosolic isoform, hCA I, also shows high affinities for both compounds ($K_I$s of 29.3-31.9 nM), although the $K_I$ values are an order of magnitude lower than that of acetazolamide. Importantly, the results show that nilotinib is a slightly better hCA I and II inhibitor compared to imatinib.

Effective inhibition with imatinib and nilotinib is also observed against the cytosolic isoform, hCA VII, the tumor-associated, transmembrane enzyme, hCA IX, and the membrane-anchored enzyme mCA XV (Table 1). These isoforms are inhibited by the two compounds with $K_I$s in the range of 41.9-109 nM. The two PTKIs show $K_I$s of 99-109 nM against the preponderantly brain-associated hCA VII, being less active than acetazolamide ($K_I$ of 2.5 nM). hCA IX is one of the most promising new anticancer drug targets as shown recently by this and other groups (Supuran, C. T. *Nat. Rev. Drug Discov.* 2008, 7, 168; Supuran, C. T. et al. *Med. Res. Rev.* 2003, 23, 146: Maresca, A. et al, *J. Am. Chem. Soc.* 2009, 131, 3057; Svastova, E. et al, *FES Lett.* 2004, 577, 439; Dubois, L.; et al, *Radiother. Oncol.* 2007, 83, 367; Hilvo, M. at al, *J. Biol. Chem.* 2008, 283, 27799; Chiche, J. et al, *J. Cancer Res.* 2009, 69, 358. The development of agents targeting this isozyme may have clinical and diagnostic significance for the management of hypoxic tumors in which CA IX is generally over-expressed (Ebbesen, P. et al. *J. Enzyme Inhib. Med. Chem.* 2009, 24 Suppl 1, 1-39). Imatinib and nilotinib significantly inhibited this isoform, with inhibition constants of 41.9-75.7 nM.

A third group of CA isozymes, including hCA III (cytosolic), VI (secreted in saliva and milk), XII (transmembrane, present in some tumors among other tissues) and XIV (transmembrane) are moderately inhibited by imatinib and nilotinib, with $K_I$s in the range of 223-980 nM. The membrane-bound hCA IV is also inhibited moderately by nilotinib ($K_I$ of 446 nM) but much less by imatinib ($K_I$ of 4553 nM, Table 1, below).

Hence, the present invention relates to imatinib and nilotinib, or pharmaceutically acceptable salts thereof, respectively, for treating disorders mediated by alpha-carbonic anhydrase isoforms.

The expression "disorders mediated by alpha-carbonic anhydrase isoforms" as used herein denotes (a) intraocular hypertension (glaucoma), epilepsy, Lennox-Gastaut syndrome, altitude sickness, migraine, headaches, gastric and duodenal ulcers, neurological disorders, obesity, and osteoporosis, and (b) cancers, especially hypoxic tumors and other cancers, in which CA II, CA IX or CA XII is overexpressed.

In one embodiment the present invention relates to the treatment of intraocular hypertension (glaucoma).

In a second embodiment the present invention relates to cancers, in which CA II is expressed. In addition to GIST (Parkkila, S. at al. 2009, unpublished results) and CML (Leppilampi, M. at al. *Clin. Cancer. Res.* 2002, 8, 2240, CA II expression has been reported in various benign tumors such as meningioma (Korhonen, K. et al. *J. Neurosurg.* 2009, Feb. 13. [Epub ahead of print]) and cancers such as pancreatic carcinoma (Parkkila, S. et al. *Histochem. J.* 1995 27, 133), glioma (Haapasalo, J. et al. *Neuro Oncol.* 2007, 9, 308, melanoma (Yoshiura, K. *Clin. Cancer Res.* 2005, 11, 8201), acute myeloid leukemia and acute lymphoblastic leukemia (Leppilampi, M. et al. *Clin. Cancer Res.* 2002). Hence, the present invention also provides for imatinib or nilotinib, or pharmaceutically acceptable salts thereof, respectively, for treating a cancer selected from GIST, CML, meningioma, pancreatic carcinoma, glioma, melanoma, acute myeloid leukemia, and acute lymphoblastic leukemia, wherein the cancer is mediated by CA II.

In a further embodiment the present invention relates to the treatment of tumors, especially hypoxic tumors, in which CA IX and/or CA XII is overexpressed.

The term "treatment" as used herein means curative treatment and prophylactic treatment.

The preparation of imatinib and its use, especially as an anti-tumor agent, are described in Example 21 of EP-A-0 564 409 and U.S. Pat. No. 5,521,184, both incorporated by reference.

Pharmaceutically acceptable salts of imatinib are pharmaceutically acceptable acid addition salts, like for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxy-ethane-sulfonic acid, or aromatic sulfonic acids, for example benzene-, p-toluene- or naphthalene-2-sulfonic acid.

The monomethanesulfonic acid addition salt of imatinib (also known as "imatinib mesylate") and preferred crystal forms thereof, e.g. the β-crystal form, are described in WO99/03854. Depending on species, age, individual condition, mode of administration, and the clinical picture in question, effective doses, for example oral daily doses of about 100-1000 mg, preferably 200-600 mg, especially 400 mg of imatinib, are administered to warm-blooded animals of about 70 kg body weight. For adult patients a starting dose corresponding to 400 mg of imatinib I free base daily can be recommended for oral delivery.

Possible pharmaceutical preparations, containing an effective amount of imatinib or a pharmaceutically acceptable salt thereof are also described in WO99/03854.

Nilotinib and the process for its manufacture are disclosed in WO 04/005281 which is incorporated by reference. Pharmaceutically acceptable salts of nilotinib are especially those disclosed in WO2007/015871. In one preferred embodiment nilotinib is employed in the form of its hydrochloride monohydrate. WO2007/015870 discloses certain polymorphs of nilotinib and pharmaceutically acceptable salts thereof useful for the present invention. A preferred oral daily dosage of nilotinib is 200-1200 mg, e.g. 800 mg, administered as a single dose or divided into multiple doses, such as twice daily dosing.

In one aspect, the present invention relates to 4-(4-methylpiperazin-1-ylmethyl)-N-[4-methyl-3-(4-pyridin-3-yl)pyrimidin-2-ylamino)phenyl]-benzamide or a pharmaceutically acceptable salt thereof, or 4-methyl-3-[[4-(3-pyridinyl)-2-pyrimidinyl]amino]-N-[5-(4-methyl-1H-imidazol-1-yl)-3-(trifluoromethyl)phenyl] benzamide or a pharmaceutically acceptable salt thereof, for the manufacture of a medicament for the treatment of disorders mediated by alpha-carbonic anhydrase isoforms.

In particular, the present invention relates to 4-(4-methylpiperazin-1-ylmethyl)-N-[4-methyl-3-(4-pyridin-3-yl)pyrimidin-2-ylamino)phenyl]-benzamide or a pharmaceutically acceptable salt thereof, especially the mesylate salt, for the treatment of disorders mediated by alpha-carbonic anhydrase isoforms.

Also, in particular, the present invention relates to 4-methyl-3-[[4-(3-pyridinyl)-2-pyrimidinyl]amino]-N-[5-(4-methyl-1H-imidazol-1-yl)-3-(trifluoromethyl)phenyl] benzamide or a pharmaceutically acceptable salt thereof, especially the hydrochloride monohydrate, for the treatment of disorders mediated by alpha-carbonic anhydrase isoforms.

More specifically, the present invention provides for 4-(4-methylpiperazin-1-ylmethyl)-N-[4-methyl-3-(4-pyridin-3-yl)pyrimidin-2-ylamino)phenyl]-benzamide or a pharmaceutically acceptable salt thereof, or 4-methyl-3-[[4-(3-pyridinyl)-2-pyrimidinyl]amino]-N-[5-(4-methyl-1H-imidazol-1-yl)-3-(trifluoromethyl)phenyl] benzamide or a pharmaceutically acceptable salt thereof, for the treatment of disorders mediated by alpha-carbonic anhydrase isoforms selected from intraocular hypertension (glaucoma), epilepsy, Lennox-Gastaut syndrome, altitude sickness, headaches, neurological disorders and obesity.

The invention relates also to a method for administering to a mammal having a disorder mediated by alpha-carbonic anhydrase isoforms a pharmaceutically effective amount of imatinib or nilotinib or a pharmaceutically acceptable salt thereof, respectively, to the human subject.

In a further embodiment, the invention relates to the following combinations and their use for treating disorders mediated by alpha-carbonic anhydrase isoforms:

(1) a combination comprising (a) imatinib or a pharmaceutically acceptable salt thereof and (b) at least one additional compound suitable for the treatment of one of the disorders mentioned herein, (2) a combination comprising (a) nilotinib or a pharmaceutically acceptable salt thereof, and (b) at least one additional compound suitable for the treatment of one of the disorders mentioned herein, (3) a combination comprising (a) imatinib or a pharmaceutically acceptable salt thereof and (b) nilotinib or a pharmaceutically acceptable salt thereof, and (4) a combination comprising (a) imatinib or a pharmaceutically acceptable salt thereof, (b) nilotinib or a pharmaceutically acceptable salt thereof, and (c) at least one additional compound suitable for the treatment of one of the disorders mentioned herein.

More specifically, the present invention relates to a combination comprising (a) 4-(4-methylpiperazin-1-ylmethyl)-N-[4-methyl-3-(4-pyridin-3-yl)pyrimidin-2-ylamino)phenyl]-benzamide or a pharmaceutically acceptable salt thereof or (b) 4-methyl-3-[[4-(3-pyridinyl)-2-pyrimidinyl]amino]-N-[5-(4-methyl-1H-imidazol-1-yl)-3-(trifluoromethyl)phenyl] benzamide or a pharmaceutically acceptable salt thereof and (c) at least one additional compound the latter being suitable for the treatment of intraocular hypertension (glaucoma), epilepsy, Lennox-Gastaut syndrome, altitude sickness, headaches, neurological disorders and obesity.

When the combination partners employed in the combinations mentioned herein are applied in the form as marketed as single drugs, their dosage and mode of administration can take place in accordance with the information provided in the prescribing information of the respective marketed drug, if not mentioned herein otherwise.

It can be demonstrated by established test models and by clinical studies that imatinib or nilotinib or a pharmaceutically acceptable salt thereof, respectively, results in an effective prevention or preferably, treatment of disorders mediated by alpha-carbonic anhydrase isoforms. The person skilled in the pertinent art is fully enabled to select a suitable test model to prove beneficial effects in the therapeutic indications mentioned herein The following Example illustrates the invention described above, but is not however, intended to limit the scope of the invention in any way.

EXAMPLE 1

Inhibition of the Catalytically Active Mammalian CA Isoforms CA I-XV by Imatinib and Nilotinib An Applied Photophysics (Oxford, UK) stopped-flow instrument is used for assaying the CA catalysed $CO_2$ hydration activity following a method described by Khalifah, R. G. *J. Biol. Chem.* 1971, 246, 2561. In brief, Phenol red (at a concentration of 0.2 mM) is used as indicator, working at the absorbance maximum of 557 nm, with 10 mM Hepes (pH 7.5) as buffer, 0.1 M $Na_2SO_4$ (for maintaining constant the ionic strength), following the CA-catalyzed $CO_2$ hydration reaction. The $CO_2$ concentrations ranges from 1.7 to 17 mM for the determination of the kinetic parameters and inhibition constants. For each inhibitor at least six traces of the initial 5-10% of the reaction are used for determining the initial velocity. The uncatalyzed rates are determined in the same manner and subtracted from the total observed rates. Stock solutions of inhibitor (10 mM) are prepared in distilled-deionized water with 5-10% (v/v) DMSO (which is not inhibitory at these concentrations) and dilutions up to 0.1 nM are done thereafter with distilled-deionized water. Inhibitor and enzyme solutions are preincubated together for 15 min at room temperature prior to assay, in order to allow for the formation of the E-I complex. The inhibition constants are obtained by non-linear least-squares methods using PRISM 3, and represent the mean from at least three different determinations. CA isozymes are recombinant ones obtained as reported earlier by (a) Pastorekova, S. at al, *J. Enz. Inhib. Med. Chem.* 2004, 19, 199; (b) Supuran, C. T., Scozzafava, A. *Bioorg. Med. Chem.* 2007, 15, 4336 (c) Nishimori, I. et al, *Bioorg. Med. Chem.* 2007, 15, 7229; (d) Vullo, D. at al, *Bioorg. Med. Chem. Lett.* 2005, 15, 971; (e) Nishimori, I. et al, *Bioorg. Med. Chem. Lett.* 2005, 15, 3828; (f) Vullo, D. at al, *Bioorg. Med. Chem. Lett.* 2005, 15, 963.

TABLE 1

Inhibition of mammalian isozymes CA I-XV (h = human, m = murine isoform) with compounds 1-3, by stopped-flow, $CO_2$ hydration assay method

| | $K_I$ (nM)[#] | | |
|---|---|---|---|
| Isozyme* | Imatinib 1 | Nilotinib 2 | Acetazolamide 3 |
| hCA I | 31.9 | 29.3 | 250 |
| hCA II | 30.2 | 4.1 | 12 |
| hCA III | 528 | 443 | 200,000 |
| hCA IV | 4,553 | 446 | 74 |
| hCA VA | 20,200 | 5,485 | 63 |
| hCA VB | 17,005 | 14,920 | 54 |
| hCA VI | 392 | 461 | 11 |
| hCA VII | 109 | 99 | 2.5 |
| hCA IX** | 75.7 | 41.9 | 25 |
| hCA XII** | 980 | 302 | 5.7 |
| mCA XIII | 7,450 | 4,665 | 17 |
| hCA XIV | 468 | 223 | 41 |
| mCA XV | 78 | 79 | 72 |

*h = human; m = murine isozyme
**Catalytic domain
[#]Mean values from three different assays, errors in the range of ±5%

The invention claimed is:

1. A method of inhibiting alpha-carbonic anhydrase isoforms in a mammal having a disorder mediated by alpha-carbonic anhydrase isoforms, the method comprising administering to the mammal having a disorder mediated by alpha-carbonic anhydrase isoforms, an effective amount of 4-(4-methylpiperazin- 1-ylmethyl)-N-[4-methyl-3 -(4-pyridin-3-yl)pyrimidin-2-ylamino)phenyl]-b enzamide or a pharmaceutically acceptable salt thereof, or 4-methyl-3-[[4-(3-pyridinyl)-2-pyri midinyl] amino] -N-[5-(4-methyl-1H-imidazol- 1-yl)-3-(trifluoromethyl)phenyl] benzamide or a pharmaceutically acceptable salt thereof, the disorder being selected from the group consisting of intraocular hypertension (glaucoma), epilepsy, Lennox-Gastaut syndrome, altitude sickness, headaches, neurological disorders, and obesity.

2. The method of claim 1, wherein the effective amount of 4-(4-methylpiperazin- 1-ylmethyl)-N- [4-methyl-3-(4-pyridin-3-yl)pyrimidin-2-ylamino)phenyl]-b enzamide or the pharmaceutically acceptable salt thereof is administered.

3. The method of claim 2, wherein the pharmaceutically acceptable salt is in the form of a mesylate salt.

4. The method of claim 1, wherein the effective amount of 4-methyl-3-[[4(3-pyridinyl))-2-pyrimidinyl]amino]-N-[5-(4-methyl-1H-imidazol-1-yl)-3-(trifluoromethyl)phenyl] benzamide or the pharmaceutically acceptable salt thereof is administered.

5. The method of claim 4, wherein the parmaceutically acceptable salt is in the form of the hydrochloride monohydrate.

6. The method of claim 1, wherein the method comprises administering a combination of 4-(4-methylpiperazin-1-ylmethyl)-N-[4-methyl-3-(4-pyridin-3-yl)pyrimidin-2-ylamino)phenyl]-b enzamide or the pharmaceutically acceptable salt thereof, and 4-methyl-3-[[4(3-pyridinyl)-2-pyrimidinyl]amino]-N-[5-(4-methyl-1H-imidazol-1-yl)-3-(trifluoromethyl)phenyl] benzamide or the pharmaceutically acceptable salt thereof.

7. A method for inhibiting alpha-carbonic anhydrase isoforms in a mammal mediated by alpha-carbonic anhydrase isoforms, the method comprising administering to the mammal having a disorder mediated by alpha-carbonic anhydrase isoforms, an effective amount of a combination comprising (a) 4-(4-methylpiperazin-1-ylmethyl)-N-[4-methyl-3-(4-pyridin-3-yl)pyrimidin-2-ylamino)phenyl]-b enzamide or a phaimaceutically acceptable salt thereof, or (b) 4-methyl-3- [[4-(3-pyridinyl)-2-pyrimidinyl]amino]-N-[5-(4-methyl-1H-imidazol-1-yl)-3-(trifluoromethyl)phenyl] benzamide or a pharmaceutically acceptable salt thereof and (c) at least one additional compound suitable for treating the disorder, the disorder being selected from the group consisting of glaucoma, epilepsy, Lennox-Gastaut syndrome, altitude sickness, headaches, neurological disorders, and obesity.

8. A method of inhibiting alpha-carbonic anhydrase isoforms in a mammal mediated by alpha-carbonic anhydrase isoforms, the method comprising administering to the mammal having the disorder mediated by alpha-carbonic anhydrase isoforms, an effective amount of 4-(4-methylpiperazin- 1-ylmethyl)-N-[4-methyl-3-(4-pyridin-3-yl)pyrimidin-2-ylamino)phenyl]-b enzamide or a pharmaceutically acceptable salt thereof, or 4-methyl-3[[4 (3-pyridinyl)-2-pyrimidinyl]amino]-N- [5-(4-methyl-1H-imidazol- 1-yl)-3-(trifluoromethyl)phenyl] benzamide or a pharmaceutically acceptable salt thereof, the disorder being selected from the group consisting of glaucoma and epilepsy.

9. The method of claim 1, wherein the disorder is glaucoma.

10. The method of claim 1, wherein the disorder is epilepsy.

11. The method of claim 1, wherein the disorder is altitude sickness.

12. The method of claim 1, wherein the disorder is headache.

13. The method of claim 1, wherein the disorder is obesity.

14. The method of claim 7, wherein the disorder is glaucoma.

15. The method of claim 7, wherein the disorder is epilepsy.

16. The method of claim 7, wherein the disorder is altitude sickness.

17. The method of claim 7, wherein the disorder is headache.

18. The method of claim 7, wherein the disorder is obesity.

19. The method of claim 7, wherein the disorder is a neurological disorder.

20. The method of claim 1, wherein the disorder is a neurological disorder.

* * * * *

UNITED STATES PATENT AND TRADEMARK OFFICE
CERTIFICATE OF CORRECTION

| | | |
|---|---|---|
| PATENT NO. | : 9,623,025 B2 | Page 1 of 1 |
| APPLICATION NO. | : 13/375946 | |
| DATED | : April 18, 2017 | |
| INVENTOR(S) | : Claudiu Supuran and Seppo Parkkila | |

It is certified that error appears in the above-identified patent and that said Letters Patent is hereby corrected as shown below:

In the Specification

Column 1,
Line 42, "c-Kit," should read --c-Kit.--.

Column 2
Line 16, "*FES*" should read --*FEBS*--.

Column 5
Line 38, "4336 (c)" should read --4336; (c)--.

Column 6
Line 28, "parmaceutically" should read --pharmaceutically--.

Column 6
Lines 35-37, "4-methyl-3-[[4(3-pyridinyl-2-pyrimidinyl]amino]-N-[5-(4-methyl-1H-imidazol-1-yl)-3-(trifluoromethyl)phenyl]" should read --4-methyl-3-[[4-(3-pyridinyl-2-pyrimidinyl]amino]-N-[5-(4-methyl-1H-imidazol-1-yl)-3-(trifluoromethyl)phenyl]--.

Column 6
Lines 62-64, "4-methyl-3[[4(3-pyridinyl)-2-pyrimidinyl]amino]-N-[5-(4-methyl-1H-imidazol-1-yl)-3-(trifluoromethyl)phenyl]" should read --4-methyl-3-[[4-(3-pyridinyl)-2-pyrimidinyl]amino]-N-[5-(4-methyl-1H-imidazol-1-yl)-3-(trifluoromethyl)phenyl]--.

Signed and Sealed this
Thirty-first Day of October, 2017

Joseph Matal
*Performing the Functions and Duties of the
Under Secretary of Commerce for Intellectual Property and
Director of the United States Patent and Trademark Office*